United States Patent
Kobayashi et al.

(10) Patent No.: US 10,364,166 B2
(45) Date of Patent: Jul. 30, 2019

(54) UV-IRRADIATION APPARATUS

(71) Applicant: Kabushiki Kaisha Toshiba, Minato-ku, Tokyo (JP)

(72) Inventors: Shinji Kobayashi, Tokyo (JP); Norimitsu Abe, Kanagawa (JP); Takeshi Ide, Tokyo (JP); Akihiko Shirota, Tokyo (JP); Kenji Takeuchi, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 14/917,914

(22) PCT Filed: Mar. 13, 2014

(86) PCT No.: PCT/JP2014/056665
§ 371 (c)(1),
(2) Date: Mar. 9, 2016

(87) PCT Pub. No.: WO2015/037260
PCT Pub. Date: Mar. 19, 2015

(65) Prior Publication Data
US 2016/0221839 A1  Aug. 4, 2016

(30) Foreign Application Priority Data
Sep. 12, 2013 (JP) .................. 2013-189323

(51) Int. Cl.
*G01J 1/42* (2006.01)
*C02F 1/32* (2006.01)
(Continued)

(52) U.S. Cl.
CPC .............. *C02F 1/325* (2013.01); *G01J 1/429* (2013.01); *G01N 21/59* (2013.01); *C02F 1/283* (2013.01);
(Continued)

(58) Field of Classification Search
CPC ............ C02F 1/325; G01J 1/429; G01N 21/59
See application file for complete search history.

(56) References Cited

U.S. PATENT DOCUMENTS

| 1,215,451 A | 2/1917 | White |
| 6,264,836 B1 * | 7/2001 | Lantis ............... C02F 1/325 |
| | | 210/188 |

(Continued)

FOREIGN PATENT DOCUMENTS

| CA | 2 894 984 A1 | 6/2014 |
| CN | 101000263 A | 7/2007 |

(Continued)

OTHER PUBLICATIONS

Notice of Reasons for Rejection dated Apr. 15, 2014 in corresponding Japanese Application No. 2013-189323, 21 pgs.

(Continued)

*Primary Examiner* — Christine S. Kim
(74) *Attorney, Agent, or Firm* — Knobbe, Martens, Olson & Bear, LLP

(57) ABSTRACT

An UV-irradiation apparatus of an embodiment is provided with an irradiation unit, a measuring unit, a detecting unit, a calculator and a display. The irradiation unit irradiates treatment water as a treatment target with treating ultraviolet rays. The measuring unit measures ultraviolet ray intensity of ultraviolet rays transmitted through the treatment water. The detecting unit detects a deterioration of the irradiation unit in accordance with the ultraviolet ray intensity measured by the measuring unit. The calculator calculates the ultraviolet ray permeability of the treatment water, on the basis of the ultraviolet ray intensity of ultraviolet rays emitted from the irradiation unit depending on a preset setting value and the ultraviolet ray intensity measured by the measuring unit. The display displays the detection result (Continued)

of the deterioration of the irradiation unit by the detecting unit, and the ultraviolet ray permeability calculated by the calculator.

5 Claims, 8 Drawing Sheets

(51) Int. Cl.
*G01N 21/59* (2006.01)
*C02F 1/28* (2006.01)
*C02F 1/52* (2006.01)
*C02F 1/76* (2006.01)

(52) U.S. Cl.
CPC ............... *C02F 1/52* (2013.01); *C02F 1/76* (2013.01); *C02F 2201/326* (2013.01); *C02F 2201/3227* (2013.01); *C02F 2209/005* (2013.01); *C02F 2209/008* (2013.01); *C02F 2303/02* (2013.01); *C02F 2303/04* (2013.01); *G01J 2001/4247* (2013.01)

(56) References Cited

U.S. PATENT DOCUMENTS

| | | | |
|---|---|---|---|
| 6,791,092 B2 * | 9/2004 | Hamilton | A61L 2/10 250/343 |
| 6,976,508 B2 | 12/2005 | Ueberall | |
| 7,385,204 B2 | 6/2008 | Bircher et al. | |
| 8,546,766 B2 * | 10/2013 | Greuel | G01F 1/68 250/373 |
| 8,552,395 B2 | 10/2013 | Kobayashi et al. | |
| 8,709,261 B2 * | 4/2014 | Levy | C02F 1/325 210/153 |
| 8,742,365 B2 | 6/2014 | Abe et al. | |
| 2003/0129105 A1 | 7/2003 | Boehme | |
| 2008/0121812 A1 | 5/2008 | Bircher | |
| 2008/0203004 A1 | 8/2008 | Abe et al. | |
| 2009/0288508 A1 | 11/2009 | Devenyi | |
| 2010/0044319 A1 * | 2/2010 | Engel | A61L 9/20 210/746 |
| 2010/0090840 A1 * | 4/2010 | Schreiner | B64D 11/02 340/600 |
| 2010/0139426 A1 | 6/2010 | Mori et al. | |
| 2011/0150708 A1 | 6/2011 | Kobayashi et al. | |
| 2012/0061585 A1 | 3/2012 | Ide et al. | |
| 2012/0235050 A1 | 9/2012 | Abe et al. | |
| 2013/0062532 A1 | 3/2013 | Abe et al. | |
| 2013/0068964 A1 | 3/2013 | Kobayashi et al. | |
| 2014/0166590 A1 * | 6/2014 | Rozenberg | C02F 1/008 210/746 |

FOREIGN PATENT DOCUMENTS

| | | |
|---|---|---|
| CN | 103837231 A | 6/2014 |
| JP | 10-057954 A | 3/1998 |
| JP | 2000-070928 A | 3/2000 |
| JP | 2001-029941 A | 2/2001 |
| JP | 2002-263645 A | 9/2002 |
| JP | 2004-049953 A | 2/2004 |
| JP | 2006-082085 A | 3/2006 |
| JP | 3881183 B2 | 2/2007 |
| JP | 4098577 B2 | 6/2008 |
| JP | 4138797 B2 | 8/2008 |
| JP | 2010-221072 A | 10/2010 |
| JP | 2011-056414 A | 3/2011 |
| JP | 2011-131138 A | 7/2011 |
| JP | 2011-131139 A | 7/2011 |
| JP | 2011-183295 A | 9/2011 |
| JP | 2011-189289 A | 9/2011 |
| JP | 2012-192381 A | 10/2012 |
| JP | 2013-059742 A | 4/2013 |
| JP | 2013-063359 A | 4/2013 |
| WO | WO 2004/033375 A1 | 4/2004 |
| WO | WO 2008/057981 A3 | 5/2008 |

OTHER PUBLICATIONS

International Search Report dated Apr. 22, 2014 in corresponding PCT Application No. PCT/JP2014/056665, 7 pgs.
Office Action mailed by Canadian Patent Office dated May 10, 2013 for Canadian patent application No. 2,784,380 in 4pgs.
Notification of the First Office Action dated Sep. 23, 2013 by State Intellectual Property Office of the People's Republic of China for Chinese patent application No. 201210268511.2 in 19 pgs.
Notification of the Second Office Action dated Apr. 28, 2014 by State Intellectual Property Office of the People's Republic of China for Chinese patent application No. 201210268511.2 in 23 pgs.
Office Action mailed by Canadian Patent Office dated May 29, 2013 for Canadian patent application No. 2,784,379 in 4 pgs.
First Office Action from the China Patent Office dated Oct. 29, 2013, regarding Chinese Patent App. No. 201210270200.X in 24 pages.
Notice of Reasons for Refusal dated Mar. 3, 2014 in Japanese Patent Application No. 2011-201839 in 5 pages.
Office Action in CA Patent Application No. 2,923,993, dated Feb. 6, 2018.

\* cited by examiner

FIG.7

| DUTY SETTING VALUE (%) | ULTRAVIOLET RAY MONITOR INDICATION VALUE S (%) | ULTRAVIOLET RAY PERMEABILITY UVT (%/cm) |
|---|---|---|
| 100 | 100 | 100.0 |
| 90 | 90 | 100.0 |
| 80 | 80 | 100.0 |
| 70 | 70 | 100.0 |
| 60 | 60 | 100.0 |
| 50 | 50 | 100.0 |
| 100 | 55.6 | 95.0 |
| 90 | 50.0 | 95.0 |
| 80 | 44.5 | 95.0 |
| 70 | 38.9 | 95.0 |
| 60 | 33.4 | 95.0 |
| 50 | 27.8 | 95.0 |
| 100 | 31.3 | 90.0 |
| 90 | 28.2 | 90.0 |
| 80 | 25.0 | 90.0 |
| 70 | 21.9 | 90.0 |
| 60 | 18.8 | 90.0 |
| 50 | 15.6 | 90.0 |
| 100 | 17.6 | 85.0 |
| 90 | 15.8 | 85.0 |
| 80 | 14.1 | 85.0 |
| 70 | 12.3 | 85.0 |
| 60 | 10.6 | 85.0 |
| 50 | 8.8 | 85.0 |
| 100 | 9.9 | 80.0 |
| 90 | 8.9 | 80.0 |
| 80 | 7.9 | 80.0 |
| 70 | 6.9 | 80.0 |
| 60 | 5.9 | 80.0 |
| 50 | 5.0 | 80.0 |
| 100 | 5.6 | 75.0 |
| 90 | 5.0 | 75.0 |
| 80 | 4.5 | 75.0 |
| 70 | 3.9 | 75.0 |
| 60 | 3.3 | 75.0 |
| 50 | 2.8 | 75.0 |
| 100 | 3.1 | 70.0 |
| 90 | 2.8 | 70.0 |
| 80 | 2.5 | 70.0 |
| 70 | 2.2 | 70.0 |
| 60 | 1.9 | 70.0 |
| 50 | 1.6 | 70.0 |

FIG.9

| DUTY SETTING VALUE (%) | ULTRAVIOLET RAY MONITOR INDICATION VALUE S (%) | ULTRAVIOLET RAY PERMEABILITY UVT (%/cm) |
|---|---|---|
| 100 | 70.0 | 97.0 |
| 90 | 63.0 | 97.0 |
| 80 | 56.0 | 97.0 |
| 70 | 49.0 | 97.0 |
| 60 | 42.0 | 97.0 |
| 50 | 35.0 | 97.0 |
| 100 | 40.1 | 92.2 |
| 90 | 36.1 | 92.2 |
| 80 | 32.0 | 92.2 |
| 70 | 28.0 | 92.2 |
| 60 | 24.0 | 92.2 |
| 50 | 20.0 | 92.2 |
| 100 | 22.9 | 87.3 |
| 90 | 20.6 | 87.3 |
| 80 | 18.3 | 87.3 |
| 70 | 16.1 | 87.3 |
| 60 | 13.8 | 87.3 |
| 50 | 11.5 | 87.3 |
| 100 | 13.1 | 82.5 |
| 90 | 11.8 | 82.5 |
| 80 | 10.5 | 82.5 |
| 70 | 9.2 | 82.5 |
| 60 | 7.9 | 82.5 |
| 50 | 6.6 | 82.5 |
| 100 | 40.1 | 92.2 |
| 90 | 36.1 | 92.2 |
| 80 | 32.0 | 92.2 |
| 70 | 28.0 | 92.2 |
| 60 | 24.0 | 92.2 |
| 50 | 20.0 | 92.2 |
| 100 | 22.9 | 87.3 |
| 90 | 20.6 | 87.3 |
| 80 | 18.3 | 87.3 |
| 70 | 16.1 | 87.3 |
| 60 | 13.8 | 87.3 |
| 50 | 11.5 | 87.3 |
| 100 | 13.1 | 82.5 |
| 90 | 11.8 | 82.5 |
| 80 | 10.5 | 82.5 |
| 70 | 9.2 | 82.5 |
| 60 | 7.9 | 82.5 |
| 50 | 6.6 | 82.5 |

UV-IRRADIATION APPARATUS

CROSS-REFERENCE TO RELATED APPLICATIONS

This application is national stage application of International Application No. PCT/JP2014/056665, filed Mar. 13, 2014, which designates the United States, incorporated herein by reference, and which claims the benefit of priority from Japanese Application No. 2013-189323, filed on Sep. 12, 2013, the entire contents of which are incorporated herein by reference.

FIELD

An embodiment described herein relates generally to an UV-irradiation apparatus.

BACKGROUND

In a conventional disinfection apparatus, in order to perform sterilization and disinfection of tap water or underground water in water and sewerage, deodorization and decoloration of industrial water, bleaching of pulp, sterilization of medical devices, and the like, chemicals such as ozone or chlorine have been used. Incidentally, in the conventional disinfection apparatus, in order to uniformly dissolve ozone and chemicals in treatment water, there has been a need for a stirring device such as a retention tank and a spray pump, it is not possible to immediately cope with changes in water quality and water quantity.

In contrast, according to a disinfection apparatus (an example of an UV-irradiation apparatus) that treats the treatment water as a treatment target using the ultraviolet rays emitted from an ultraviolet ray lamp, it is possible to perform sterilization, disinfection and decoloration of tap water or underground water in the water and sewerage, deodorization and decoloration of industrial water, bleaching of pulp, and the like, and it is also possible to immediately cope with changes in water quality and water quantity by regulating the output of the ultraviolet ray lamp.

However, in the conventional UV-irradiation apparatus, in order to monitor whether ultraviolet rays with ultraviolet ray intensity required for treatment of the treatment water are emitted from the ultraviolet ray lamp, the ultraviolet ray permeability of the treatment water is measured by a dedicated measuring device, and it is determined whether the ultraviolet ray intensity emitted from the ultraviolet ray lamp satisfies a prescribed value defined by the operation specification of the UV-irradiation apparatus, based on the measurement result.

BRIEF DESCRIPTION OF DRAWINGS

FIG. 7 is a diagram illustrating a calculation result of the ultraviolet ray permeability according to Formula (2) that uses the ultraviolet ray monitor indication value and the duty setting value;

FIG. 9 is a diagram illustrating the calculation results of the ultraviolet ray permeability when the ultraviolet ray monitor indication value is lowered to 70% due to a deterioration of an irradiation unit of the UV-irradiation apparatus according to the third embodiment.

DETAILED DESCRIPTION

In general, an according to an embodiment, an UV-irradiation apparatus is provided with an irradiation unit, a measuring unit, a detecting unit, a calculator and a display. The irradiation unit irradiates treatment water as a treatment target with treating ultraviolet rays. The measuring unit measures ultraviolet ray intensity of ultraviolet rays transmitted through the treatment water. The detecting unit detects a deterioration of the irradiation unit in accordance with the ultraviolet ray intensity measured by the measuring unit. The calculator calculates the ultraviolet ray permeability of the treatment water, on the basis of the ultraviolet ray intensity of ultraviolet rays emitted from the irradiation unit depending on a preset setting value and the ultraviolet ray intensity measured by the measuring unit. The display displays the detection result of the deterioration of the irradiation unit by the detecting unit, and the ultraviolet ray permeability calculated by the calculator.

Hereinafter, a tap water treatment system provided with an UV-irradiation apparatus according to this embodiment will be described with reference to the accompanying drawings.

First Embodiment

Figure 1:
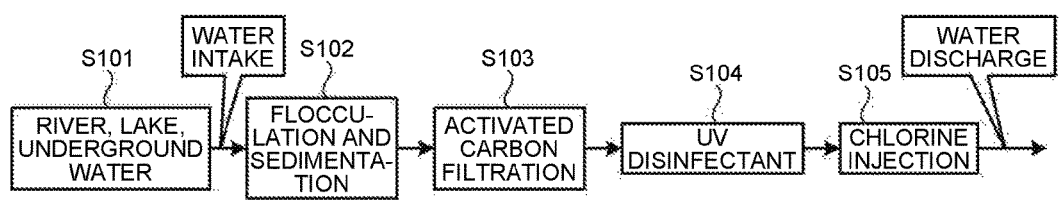
FIG. 1 is a flowchart illustrating a treatment process of treatment water in a tap water treatment system according to a first embodiment.

First, an outline of a flow of treatment in the tap water treatment system according to this embodiment will be described with reference to FIG. 1. FIG. 1 is a flowchart illustrating the treatment process of the treatment water in the tap water treatment system according to the first embodiment. As illustrated in FIG. 1, the tap water treatment system according to this embodiment takes raw water (an example of the treatment water as a treatment target) from river, lake or underground water or the like (step S101). Next, the tap water treatment system introduces the intake raw water into a flocculation and sedimentation tank, and flocculates and sediments the raw water by adding a coagulant thereto (step S102). Next, as illustrated in FIG. 1, the tap water treatment system sends the supernatant water in the flocculation and sedimentation tank to an activated carbon filtration tank to filter foreign matters (step S103). Moreover, the tap water treatment system sends the filtered water to an UV-irradiation apparatus 1 (see FIG. 2) to irradiate the filtered water with ultraviolet rays (step S104), sends the UV disinfectant treatment water irradiated with ultraviolet rays to a chlorine injection tank to inject chlorine into the treatment water (step S105), and thereafter, distributes water to general home, office, or the like.

Figure 2:
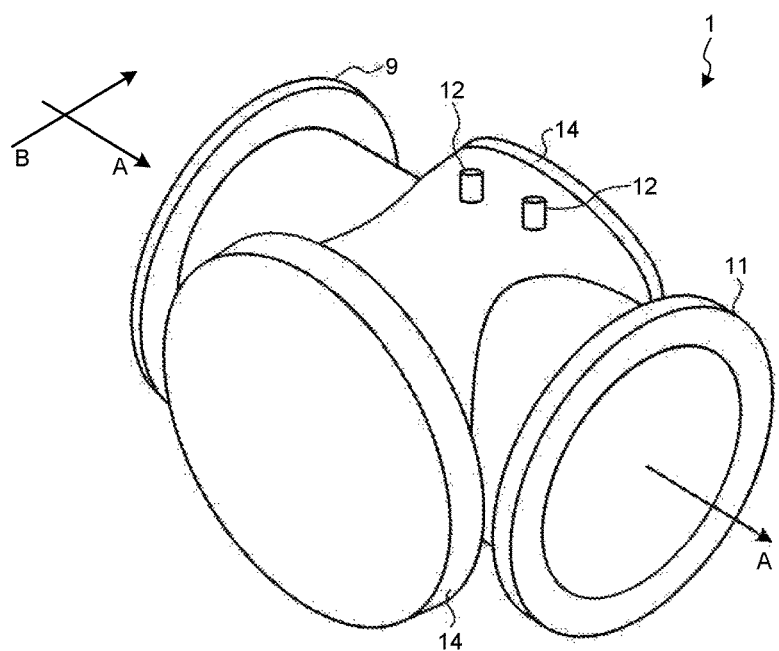
FIG. 2 is an external view of an UV-irradiation apparatus according to the first embodiment.
Figure 3:
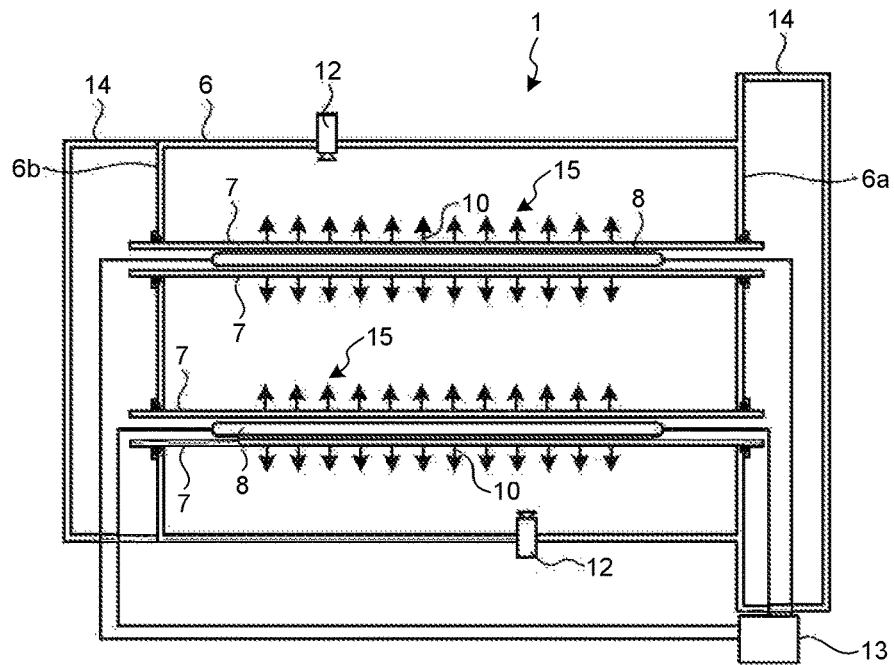
FIG. 3 is a vertical cross-sectional view of a reaction tank provided in the UV-irradiation apparatus according to the first embodiment.
Figure 4:
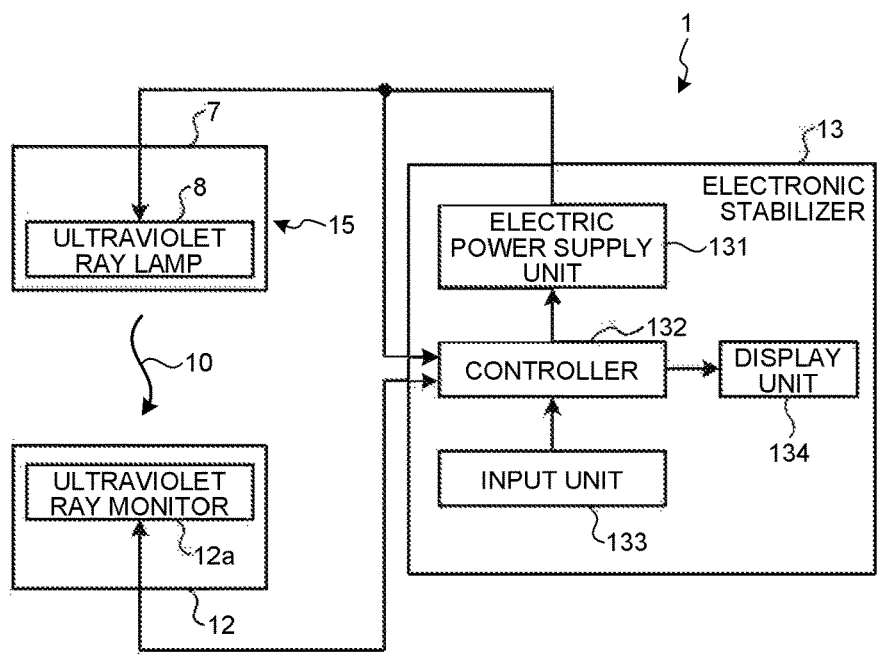
FIG. 4 is a block diagram illustrating a hardware configuration of an electronic stabilizer provided in the UV-irradiation apparatus according to the first embodiment.

Next, an UV-irradiation apparatus according to this embodiment will be described with reference to FIGS. 2 to 4. FIG. 2 is an external view of the UV-irradiation apparatus according to the first embodiment. FIG. 3 is a vertical cross-sectional view of a reaction tank provided in the UV-irradiation apparatus according to the first embodiment. FIG. 4 is a block diagram illustrating a hardware configuration of an electronic stabilizer provided in the UV-irradiation apparatus according to the first embodiment.

The UV-irradiation apparatus 1 performs sterilization, disinfection, inactivation, or the like of the treatment water by irradiating the treatment water with treating ultraviolet rays. In this embodiment, the UV-irradiation apparatus 1 is provided with a reaction tank (a treatment tank) 6 through which the treatment water passes, a water supply port 9, a water discharge port 11, a protective tube 7, an ultraviolet ray monitor window 12 and a protective cover 14.

The reaction tank 6 allows the treatment water for performing the sterilization, the disinfection and the inactivation to pass therethrough. Further, the reaction tank 6 has a water inlet that supplies (flows in) the treatment water, and a water outlet that discharges (flows out) the treatment water subjected to treatment. The water inlet and the water outlet are formed to face each other in the reaction tank 6. Further, the water supply port 9 is connected to the water inlet of the reaction tank 6. Moreover, the water discharge port 11 is connected to the water outlet of the reaction tank 6. The treatment water passes to flow in a direction toward the water outlet (the water discharge port 11) from the water inlet (the water supply port 9), that is, in an A direction of FIG. 2. Further, a horizontal direction perpendicular to the A direction is set as a B direction.

The protective tube 7, for example, is formed of a member such as a quartz glass permeable to ultraviolet rays. Further, as illustrated in FIG. 3, an ultraviolet ray lamp 8 is housed inside the protective tube 7, and the ultraviolet ray lamp 8 irradiates the treatment water that passes toward the water outlet from the water inlet with the treating ultraviolet rays. A wiring for supplying electricity to the ultraviolet ray lamp 8 from both ends is connected to the ultraviolet ray lamp 8, and the ultraviolet ray lamp 8 is connected to an electronic stabilizer 13 that supplies electric power to the ultraviolet ray lamp 8 via the wiring.

Further, the protective tube 7 is provided inside the reaction tank 6 in a direction that intersects with the direction toward the water outlet from the water inlet. In this embodiment, in the UV-irradiation apparatus 1, each of the two protective tubes 7 arranged side by side in a direction toward the water outlet from the water inlet (a direction in which the treatment water passes) is provided above and below the reaction tank 6. In this embodiment, the ultraviolet ray lamp 8 and the protective tube 7 function as an irradiation unit 15.

An ultraviolet ray monitor 12a (an example of a measuring unit) is installed in an ultraviolet ray monitor window 12, and the ultraviolet ray monitor 12a measures the ultraviolet ray intensity of ultraviolet rays emitted from the ultraviolet ray lamp 8 and transmitted through the treatment water. In this embodiment, each of the two ultraviolet ray monitor windows 12 is vertically provided with the protective tubes 7 formed inside the reaction tank 6 interposed therebetween.

The electronic stabilizer 13 is provided with an electric power supply unit 131 capable of supplying electric power to the ultraviolet ray lamp 8, a controller 132 that controls the entire electronic stabilizer 13, an input unit 133 capable of inputting various kinds of information to the electronic stabilizer 13 (for example, a rating of the ultraviolet ray lamp 8, a distance between the irradiation unit 15 and the ultraviolet ray monitor 12a, and sensitivity of the ultraviolet ray monitor 12a), and a display 134 capable of displaying various kinds of information (for example, the detection result of the deterioration of the irradiation unit 15, the ultraviolet ray permeability of the treatment water passing through the reaction tank 6, and the like).

The protective cover 14 shields ultraviolet rays 10 emitted from the irradiation unit 15. In this embodiment, the protective cover 14 is provided outside a side surface 6a and a side surface 6b of the reaction tank 6.

Figure 5:
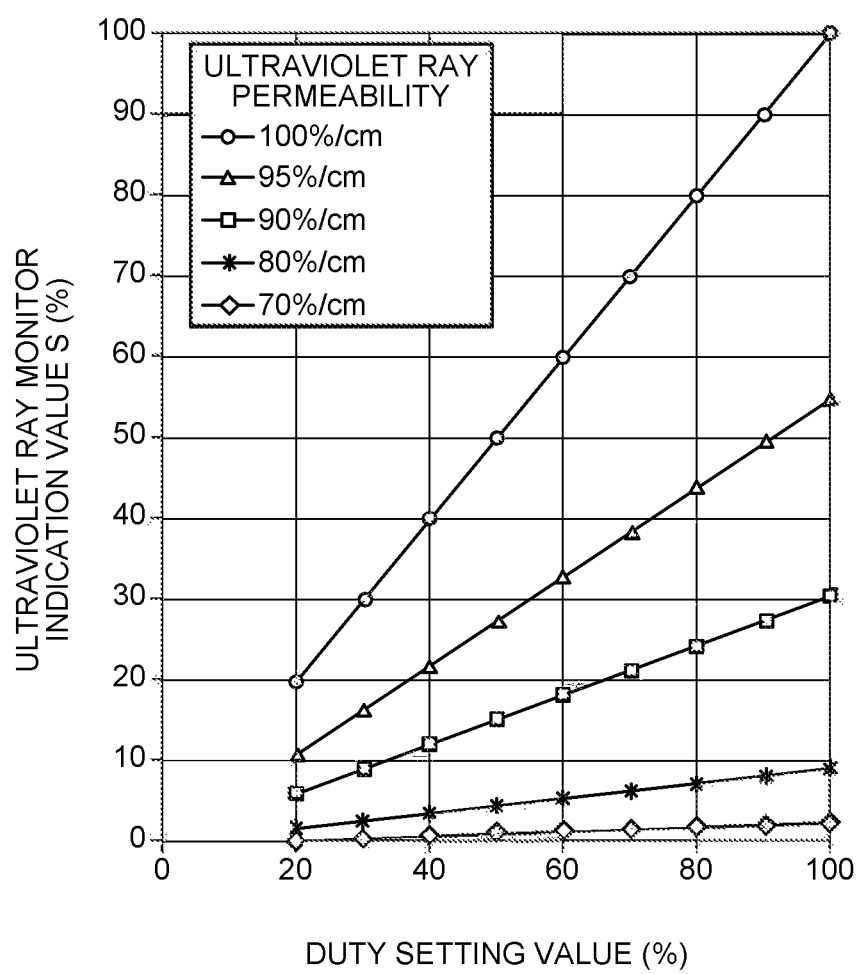
FIG. 5 is a diagram illustrating a relation between an ultraviolet ray monitor indication value and a duty setting value.
Figure 6:
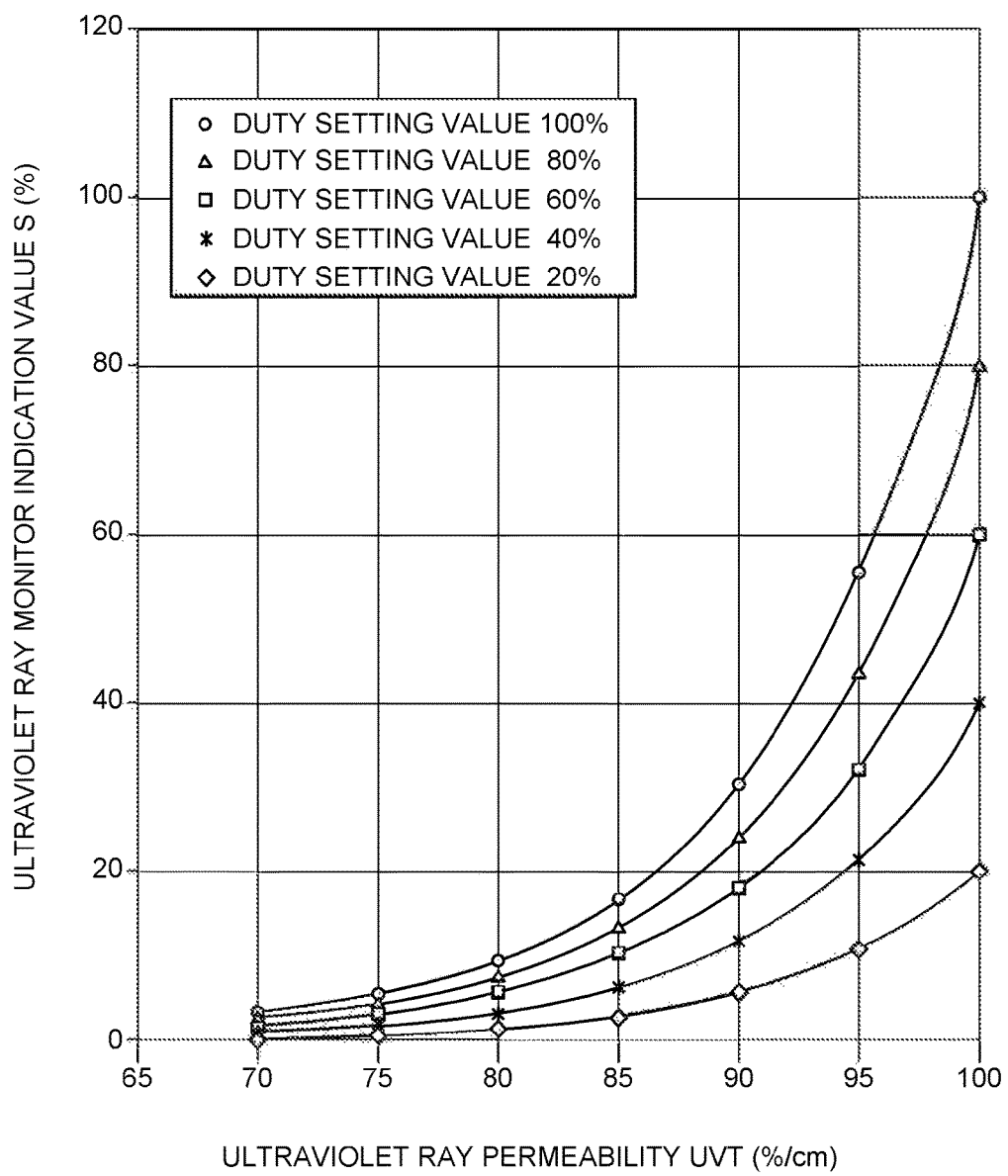
FIG. 6 is a diagram illustrating a relation between the ultraviolet ray monitor indication value and ultraviolet ray permeability when the water quality or the like of the treatment water passing through the reaction tank changes.

Next, in the UV-irradiation apparatus 1 according to this embodiment, the treatment indicating the detection result of the deterioration of the ultraviolet ray lamp 8 and the ultraviolet ray permeability of the treatment water passing through the reaction tank 6 will be described with reference to FIGS. 4 to 7. FIG. 5 is a diagram illustrating a relation between an ultraviolet ray monitor indication value and a duty setting value. FIG. 6 is a diagram illustrating a relation between the ultraviolet ray monitor indication value and the ultraviolet ray permeability when the water quality or the like of the treatment water passing through the reaction tank changes. FIG. 7 is a diagram illustrating a calculation result of the ultraviolet ray permeability according to Formula (2) that uses the ultraviolet ray monitor indication value and the duty setting value.

When the start instruction instructing the start of the irradiation of ultraviolet rays to the treatment water is input via the input unit 133, the controller 132 controls the electric power supply unit 131 to supply electric power to the ultraviolet ray lamp 8, and starts the irradiation of treating ultraviolet rays to the treatment water that passes through the reaction tank 6. In this embodiment, the controller 132 outputs a pulse signal (hereinafter, referred to as a variable duty pulse signal) for adjusting the ultraviolet ray intensity of ultraviolet rays emitted from the ultraviolet ray lamp 8 to the electric power supply unit 131, in accordance with a duty ratio (hereinafter, referred to as a duty setting value) that is input from the input unit 133s Accordingly, the controller 132 adjusts the ultraviolet ray intensity of ultraviolet rays emitted from the irradiation unit 15. That is, the irradiation unit 15 emits ultraviolet rays depending on the duty setting value (a preset setting value).

When the irradiation of ultraviolet rays to the treatment water is started, the ultraviolet ray monitor 12a measures the ultraviolet ray intensity of ultraviolet rays transmitted through the treatment water. Further, when the ultraviolet ray lamp 8 does not deteriorate and the ultraviolet ray permeability UVT of the treatment water is 100%/cm, the ultraviolet ray monitor 12a calculates a ratio (hereinafter, referred to as an ultraviolet ray monitor indication value) of the ultraviolet ray intensity of ultraviolet rays transmitted through the treatment water relative to the ultraviolet ray intensity of the ultraviolet rays emitted from the ultraviolet ray lamp 8 depending on the duty setting value: the variable duty pulse signal of 100%.

The controller 132 (the detecting unit) detects the deterioration of the irradiation unit 15 in accordance with the ultraviolet ray intensity measured by the ultraviolet ray monitor 12a. In this embodiment, the controller 132 detects that the irradiation unit 15 deteriorates when the ultraviolet ray monitor indication value calculated by the ultraviolet ray monitor 12a is lowered to a predetermined value in which the treatment performance (for example, the disinfection performance or the like) to the treatment water cannot be maintained.

Further, the controller 132 (the calculator) calculates the ultraviolet ray permeability UVT of ultraviolet rays to the treatment water, on the basis of the ultraviolet ray intensity of ultraviolet rays emitted from the irradiation unit 15 depending on the duty setting value and the measured ultraviolet ray intensity (ultraviolet ray intensity of ultraviolet rays transmitted through the treatment water). In this embodiment, the controller 132 calculates the ultraviolet ray permeability UVT, on the basis of the duty setting value and the ultraviolet ray lamp indication value S measured by the ultraviolet ray monitor 12a.

As illustrated in the following Formula (1), the ultraviolet ray monitor indication value S (%) measured by the ultraviolet ray monitor 12a is represented by a function between a change value F (UVT) that is a ratio representing the ultraviolet ray permeability UVT of the treatment water and the lamp input value D that is a ratio representing the duty setting value.

$$S = F(UVT) \times S_{100} \times D \qquad (1)$$

Here, $S_{100}$ is an ultraviolet ray monitor indication value S (100%) in the case where the ultraviolet ray lamp 8 does not deteriorate, the ultraviolet ray permeability UVT is 100%/cm, and the duty setting value is 100%.

Therefore, when there is no change in the ultraviolet ray permeability UVT (that is, when there is no change in the water quality or the like of the treatment water that passes through the reaction tank 6), the ultraviolet ray monitor indication value S increases in proportion to the duty setting value. A relation between the ultraviolet ray monitor indication value S and the duty setting value is represented by a linear function passing through an origin, as illustrated in FIG. 5.

Meanwhile, when the duty setting value is constant and the ultraviolet ray permeability UVT changes (for example, when the water quality or the like of the treatment water passing through the reaction tank 6 changes), as illustrated in FIG. 6, the ultraviolet ray monitor indication value S exponentially changes with respect to changes in the ultraviolet ray permeability UVT. Thus, as long as the ultraviolet ray monitor indication value S and the duty setting value can be specified, the ultraviolet ray permeability UVT can be calculated by Formula (2). In this embodiment, the controller 132 calculates the ultraviolet ray permeability UVT by Formula (2), using the ultraviolet ray monitor indication value S and the duty setting value.

$$UVT = A \times \ln(B \times S/D) \qquad (2)$$

Here, A and B are predetermined coefficients, and in this embodiment, A=8.8588, and B=10000.

As illustrated in FIG. 7, the ultraviolet ray monitor indication value S exponentially changes with respect to a change in ultraviolet ray permeability UVT calculated by Formula (2). That is, according to Formula (2), when the duty setting value is constant, it is possible to calculate the ultraviolet ray monitor indication value S that exponentially changes with respect to a change in the ultraviolet ray permeability UVT.

Further, the controller 132 displays the detection results of the deterioration of the irradiation unit 15 (for example, a decrease in ultraviolet ray monitor indication value S to a predetermined value or less in which the treatment performance to the treatment water cannot be maintained), and the calculated ultraviolet ray permeability UVT on a display 134.

With the UV-irradiation apparatus 1 according to the first embodiment, by calculating the ultraviolet ray permeability UVT on the basis of the ultraviolet ray intensity of treating ultraviolet rays with which the treatment water from the irradiation unit 15 is irradiated depending on the duty setting value, and the ultraviolet ray intensity of ultraviolet rays transmitted through the treatment water, since there is no need to provide a dedicated measuring device capable of measuring the ultraviolet ray permeability, it is possible to calculate the ultraviolet ray permeability UVT of the treatment water at a low cost and with a simple configuration.

Second Embodiment

This embodiment is an example of detecting the deterioration of the irradiation unit in accordance with the ultraviolet ray intensity of ultraviolet rays transmitted through the treatment water and the calculated ultraviolet ray permeability. In the following description, the description of the same parts as in the first embodiment will not be provided.

A controller 132 (a detecting unit) detects the deterioration of the irradiation unit 15 in accordance with the ultraviolet ray intensity (in this embodiment, the ultraviolet ray monitor indication value S) of ultraviolet rays transmitted through the treatment water, and the calculated ultraviolet ray permeability UVT. Specifically, when the measured ultraviolet ray monitor indication value S is lowered to a predetermined value or less in which the treatment performance to the treatment water cannot be maintained and the calculated ultraviolet ray permeability UVT is equal to or less than a preset permeability, there is a high possibility that the ultraviolet ray monitor indication value S is lowered due to the temporary deterioration of the water quality of treatment water. Therefore, in this case, the controller 132 does not detect that the measured ultraviolet ray monitor indication value S becomes equal to or less than a predetermined value as the deterioration of the irradiation unit 15.

Meanwhile, when the measured ultraviolet ray monitor indication value S is lowered to a predetermined value or less and the calculated ultraviolet ray permeability UVT is higher than the predetermined permeability, there is a high possibility that the ultraviolet ray monitor indication value S is lowered due to the deterioration of the ultraviolet ray lamp 8 and the protective tube 7. Therefore, in this case, the controller 132 detects that the measured ultraviolet ray monitor indication value S becomes equal to or less than the predetermined value as the deterioration of the irradiation unit 15.

In this way, with the UV-irradiation apparatus 1 according to the second embodiment, by detecting the deterioration of the irradiation unit 15 in accordance with the ultraviolet ray intensity of ultraviolet rays transmitted through the treatment water and the calculated ultraviolet ray permeability UVT, when the ultraviolet ray monitor indication value S is lowered due to the temporary deterioration of the water quality of the treatment water, since the measured ultraviolet ray monitor indication value S becoming equal to or less than a predetermined value is not detected as the deterioration of the irradiation unit 15, it is possible to improve the detection precision of the deterioration of the irradiation unit 15.

Third Embodiment

This embodiment is an example in which an ultraviolet ray monitor is disposed to be spaced apart from the irradiation unit so that a displacement amount of the ultraviolet ray permeability due to the deterioration of the irradiation unit and the ultraviolet ray monitor becomes equal to or less than an allowable error. In the following description, the description of the same parts as the above embodiment will not be provided.

Figure 8:
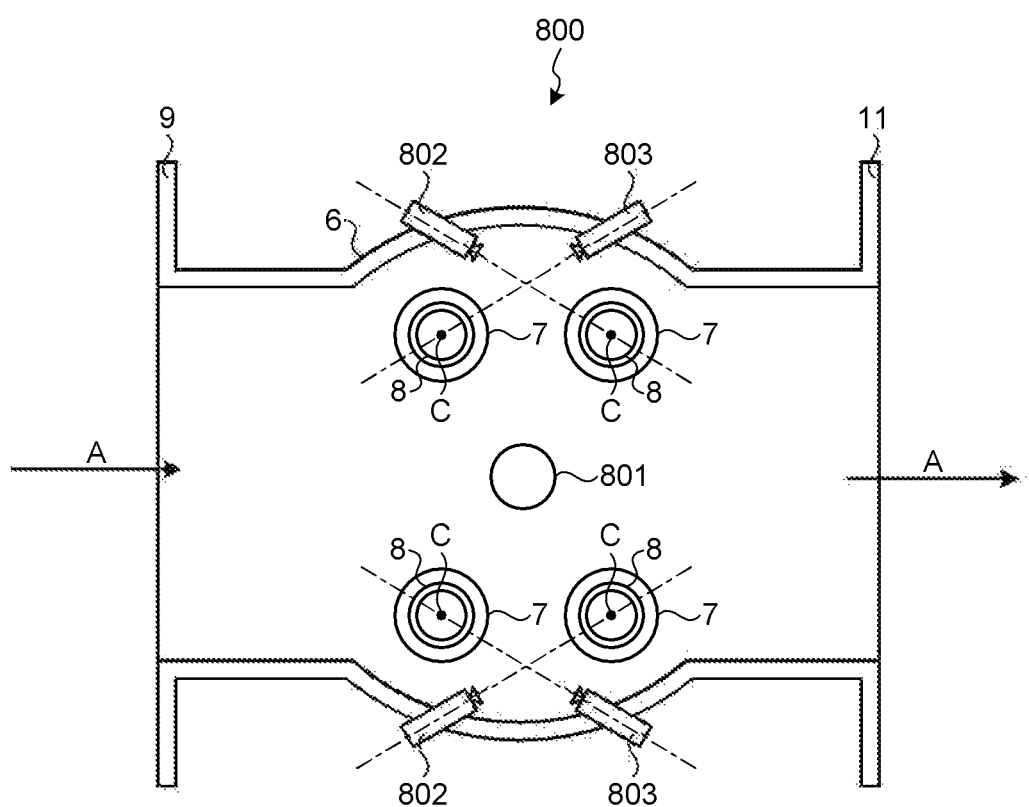
FIG. 8 is a vertical cross-sectional view of a reaction tank provided in an UV-irradiation apparatus according to a third embodiment.

FIG. 8 is a vertical cross-sectional view of a reaction tank provided in the UV-irradiation apparatus according to the third embodiment. As illustrated in FIG. 8, in an UV-irradiation apparatus 800 according to this embodiment, a guide rod 801 that supports a cleaning unit (not illustrated) movably provided along the protective tube 7 to remove dirt adhering to an outer surface of the protective tube 7 is provided in parallel to the protective tube 7.

Further, in the UV-irradiation apparatus 800 according to this embodiment, each of two ultraviolet ray monitor windows 802 and 803 disposed side by side in a direction toward the water outlet from the water inlet (a flow direction of the treatment water) is provided above and below the reaction tank 6. Further, an ultraviolet ray monitor window 803 (an ultraviolet ray monitor 12a) disposed on a downstream side in the flow direction of the treatment water is disposed to measure the ultraviolet ray intensity of ultraviolet rays emitted from the irradiation unit 15 disposed on the upstream side in the flow direction of the treatment water. More specifically, the ultraviolet ray monitor window 803 is provided toward the central axis C of the protective tube 7 (the ultraviolet ray lamp 8) which is disposed on the upstream side in the flow direction of the treatment water. Meanwhile, the ultraviolet ray monitor window 802 (the ultraviolet ray monitor 12a) disposed on the upstream side in the flow direction of the treatment water is disposed to measure the ultraviolet ray intensity of ultraviolet rays emitted from the irradiation unit 15 disposed on the downstream side in the flow direction of the treatment water. More specifically, the ultraviolet ray monitor window 802 is provided toward the central axis C of the protective tube 7 (the ultraviolet ray lamp 8) which is disposed on the downstream side in the flow direction of the treatment water.

Thus, the ultraviolet ray monitor windows 802 and 803 (the ultraviolet ray monitor 12a) are disposed to be spaced apart from the irradiation unit 15 so that a displacement amount of the ultraviolet ray permeability UVT due to the deterioration of the irradiation unit 15 and the ultraviolet ray monitor windows 802 and 803 (the ultraviolet ray monitor 12a) becomes equal to or less than an allowable error. Specifically, the ultraviolet ray monitor windows 802 and 803 are disposed to be spaced apart from the irradiation unit 15 so that the displacement amount of the ultraviolet ray permeability UVT becomes equal to or less than an allowable error when the ultraviolet ray intensity (in this embodiment, the ultraviolet ray monitor indication value S) of ultraviolet rays transmitted through the treatment water is lowered to a predetermined value. For example, when the allowable error of ultraviolet ray permeability UVT″ is 3%, a distance (a liquid phase distance) n between the ultraviolet ray monitor windows 802 and 803 and the irradiation unit 15 is calculated by the following Formula (3).

$$UVT''=(1-0.03)^n=0.97^n \geq 0.7 \quad (3)$$

n≥11.5 (cm)

Here, 0.7 is a ratio that represents a predetermined value (for example, 70%) in which the treatment performance to the treatment water cannot be maintained.

In this embodiment, the ultraviolet ray monitor window 803 is disposed to measure the ultraviolet ray intensity of ultraviolet rays emitted from the irradiation unit 15 disposed on the upstream side, and the ultraviolet ray monitor window 802 is disposed to measure the ultraviolet ray intensity of ultraviolet rays emitted from the irradiation unit 15 disposed on the downstream side. However, as long as the ultraviolet ray monitor windows 802 and 803 are disposed so that the displacement amount of the ultraviolet ray permeability UVT due to the deterioration of the irradiation unit 15 and the ultraviolet ray monitor windows 802 and 803 (the ultraviolet ray monitor 12a) becomes equal to or less than an allowable error, the embodiment is not limited thereto. For example, the ultraviolet ray monitor window 803 may be provided to measure the ultraviolet ray intensity of ultraviolet rays emitted from the irradiation unit 15 disposed on the downstream side, and the ultraviolet ray monitor window 802 may be provided to measure the ultraviolet ray intensity of ultraviolet rays emitted from the irradiation unit 15 disposed on the upstream side.

FIG. 9 is a diagram illustrating the calculation results of the ultraviolet ray permeability when the ultraviolet ray monitor indication value is lowered to 70% due to the deterioration of the irradiation unit of the UV-irradiation apparatus according to the third embodiment. In the UV-irradiation apparatus 800, by its operational history, the ultraviolet ray monitor indication value S (the measurement result of the ultraviolet ray intensity of ultraviolet rays transmitted through the treatment water) measured by the ultraviolet ray monitor 12a is lowered, due to a decrease in ultraviolet ray intensity of ultraviolet rays emitted from the ultraviolet ray lamp 8 caused by deterioration of the ultraviolet ray lamp 8, a decrease in permeability of ultraviolet rays of the protective tube 7 caused by the deterioration of the protective tube 7, the dirt adhering to the protective tube 7, the dirt of the ultraviolet ray monitor windows 802 and 803 and the like. The ultraviolet ray lamp 8, the protective tube 7 and the ultraviolet ray monitor windows 802 and 803 are consumable, and are exchanged as lifetime when the measured ultraviolet ray monitor indication value S is lowered to a predetermined value (in this embodiment, 70%) or less in which the treatment performance of the treatment water cannot be maintained.

Here, as described above, the ultraviolet ray monitor windows 802 and 803 are provided to be spaced apart from the irradiation unit 15 so that the displacement amount of the ultraviolet ray permeability UVT becomes equal to or less than the allowable error (3%) when the ultraviolet ray monitor indication value S is lowered to 70%. Therefore, even when the ultraviolet ray monitor indication value S is lowered to 70%, as illustrated in FIG. 9, the displacement amount of the ultraviolet ray permeability UVT calculated by the controller 132 becomes equal to or less than an allowable error (3%), as compared to the ultraviolet ray permeability UVT (see FIG. 7) when the ultraviolet ray monitor indication value S is 100%. Thus, even when the ultraviolet ray monitor indication value S is lowered due to the deterioration of the irradiation unit 15 and the ultraviolet ray monitor windows 802 and 803 (the ultraviolet ray monitor 12a), since it is possible to obtain the ultraviolet ray permeability UVT in which the displacement amount is equal to or less than the allowable error, it is possible to calculate the ultraviolet ray permeability UVT with the reduced influence due to the deterioration of the irradiation unit 15 or the like.

According to the UV-irradiation apparatus 800 of the third embodiment, since the ultraviolet ray monitor 12a is disposed to be spaced apart from the irradiation unit 15 so that the displacement amount of the ultraviolet ray permeability UVT due to the deterioration of the irradiation unit 15 and the ultraviolet ray monitor windows 802 and 803 (the ultraviolet ray monitor 12a) becomes equal to or less than an allowable error, even when the ultraviolet ray intensity measured by the ultraviolet ray monitor 12a is lowered due to the deterioration of the irradiation unit 15 and the ultraviolet ray monitor windows 802 and 803 (the ultraviolet ray monitor 12a), it is possible to obtain the ultraviolet ray permeability UVT with a displacement amount equal to or less than an allowable error. Thus, it is possible to calculate the ultraviolet ray permeability UVT with the reduced influence due to the deterioration of the irradiation unit 15 and the ultraviolet ray monitor windows 802 and 803 (the ultraviolet ray monitor 12a).

Fourth Embodiment

This embodiment is an example that calculates the effective irradiation intensity of the treating ultraviolet rays emitted from the irradiation unit and the effective transmission intensity measured by the ultraviolet ray monitor, using the permeability of ultraviolet rays to the treatment water measured by an external measuring device, and calculates the ultraviolet ray permeability based on the calculated effective irradiation intensity and effective transmission intensity. In the following description, the description of the same parts as in the above embodiments will not be provided.

Figure 10:
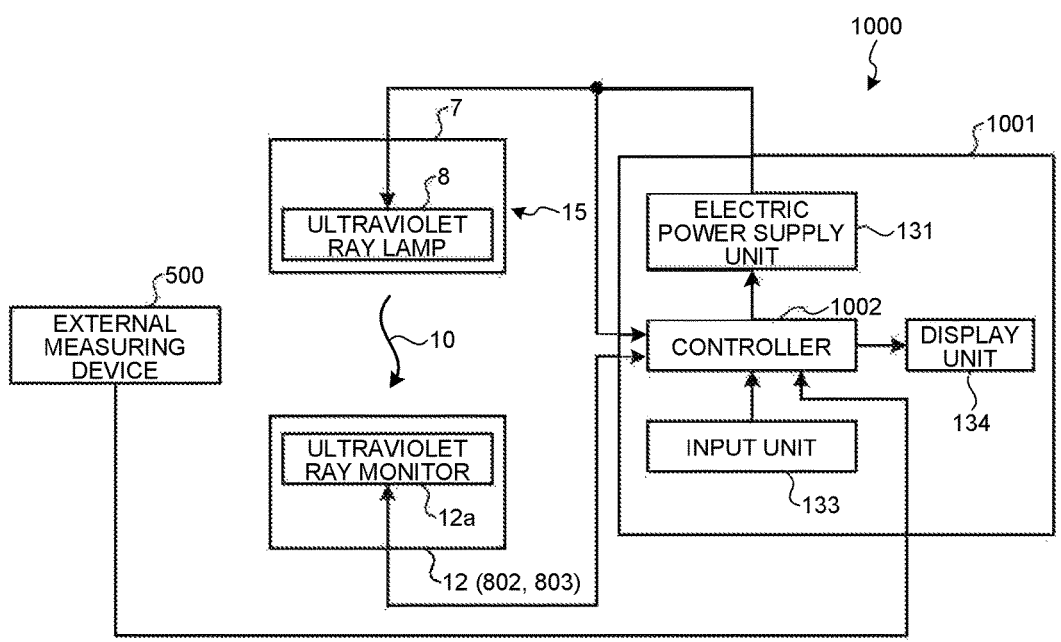
FIG. 10 is a block diagram illustrating a hardware configuration of an electronic stabilizer provided in an UV-irradiation apparatus according to a fourth embodiment.

FIG. 10 is a block diagram illustrating a hardware configuration of an electronic stabilizer provided in an UV-irradiation apparatus according to a fourth embodiment. An electronic stabilizer 1001 provided in an UV-irradiation apparatus 1000 according to this embodiment is provided with an electric power supply unit 131, an input unit 133, a display 134 and a controller 1002. In this embodiment, the controller 1002 calculates the effective irradiation intensity of the treating ultraviolet rays emitted from the irradiation unit 15 and the effective transmission intensity measured by the ultraviolet ray monitor 12a, using the permeability (hereinafter, referred to as deterioration coefficient K) of ultraviolet rays to the treatment water measured by an external measuring device 500, and calculates the ultraviolet ray permeability UVT on the basis of the calculated effective irradiation intensity and the effective transmission intensity.

Here, the effective irradiation intensity is the ultraviolet ray intensity of ultraviolet rays with which the treatment water is irradiated (in this embodiment, the ultraviolet ray intensity of ultraviolet rays corresponding to the lamp input value D that is a ratio representing the duty setting value), in consideration of a decrease in ultraviolet ray intensity of ultraviolet rays emitted from the ultraviolet ray lamp 8, a decrease in the permeability of ultraviolet rays of the protective tube 7 and the like. Further, the effective transmission intensity is ultraviolet ray intensity of ultraviolet rays transmitted through the treatment water, in consideration of a decrease in the ultraviolet ray intensity (in this embodiment, the ultraviolet ray monitor indication value S) measured by the ultraviolet ray monitor 12a.

In this embodiment, the controller 1002 calculates the ultraviolet ray permeability UVT, using the deterioration coefficient K as the permeability of ultraviolet rays measured by the external measuring device 500, the lamp input value D and the ultraviolet ray monitor indication value S in accordance with the following Formulas (4) and (5).

$$K = S/(UVT, D, S) = S/(1/B \times \exp(UVT \times D/A)) \quad (4)$$

$$UVT = A \times \ln(B \times S/D/K) \quad (5)$$

Thus, according to the UV-irradiation apparatus 1000 of the fourth embodiment, the effective irradiation intensity of the treating ultraviolet ray emitted from the irradiation unit 15 and the effective transmission intensity measured by the ultraviolet ray monitor 12a are calculated, using the permeability of ultraviolet rays to the treatment water (the deterioration coefficient K) measured by the external measuring device 500, and the ultraviolet ray permeability UVT is calculated based on the calculated effective irradiation intensity and effective transmission intensity. Thus, it is possible to calculate the ultraviolet ray permeability UVT with the reduced influences of a decrease in ultraviolet ray intensity of ultraviolet rays emitted from the ultraviolet ray lamp 8, a decrease in permeability of the ultraviolet rays of the protective tube 7 and a decrease in ultraviolet ray intensity measured by the ultraviolet ray monitor 12a.

In the above-described embodiment, although the UV-irradiation apparatuses 1, 800 and 1000 calculate the ultraviolet ray permeability UVT, based on the measurement result of the ultraviolet ray intensity of ultraviolet rays by the ultraviolet ray monitor 12a used for detecting the deterioration of the irradiation unit 15, the embodiment is not limited thereto. For example, the UV-irradiation apparatuses 1, 800 and 1000 are provided with a second measuring unit that measures the ultraviolet ray intensity of ultraviolet rays transmitted through the treatment water apart from the ultraviolet ray monitor 12a, and the controllers 132 and 1002 (calculators) may calculate the ultraviolet ray permeability, based on the ultraviolet ray intensity of ultraviolet rays emitted from the irradiation unit 15 and the ultraviolet ray intensity measured by the second measuring unit. Accordingly, since it is possible to measure the ultraviolet ray intensity of ultraviolet rays transmitted through the treatment water without being affected by the deterioration of the ultraviolet ray monitor 12a, it is possible to improve the calculation precision of the ultraviolet ray permeability UVT.

In the above-described embodiments, although the UV-irradiation apparatuses 1, 800 and 1000 calculate the ultraviolet ray permeability UVT based on the ultraviolet ray intensity of ultraviolet rays from the irradiation unit 15 that emits treating ultraviolet rays, the embodiment is not limited thereto. For example, the UV-irradiation apparatuses 1, 800 and 1000 are provided with a second irradiation unit that irradiates the treatment water with ultraviolet rays for calculating the ultraviolet ray permeability UVT, apart from the irradiation unit 15, in addition to the second measuring unit, and the controllers 132 and 1002 (the calculators) may calculate the ultraviolet ray permeability UVT on the basis of the ultraviolet intensity of ultraviolet rays emitted from the second irradiation unit and the ultraviolet intensity measured by the second measuring unit. Thus, since it is possible to irradiate the treatment water with ultraviolet rays for calculating of the ultraviolet ray permeability UVT, without being affected by the deterioration of the irradiation unit 15, it is possible to improve the calculation precision of the ultraviolet ray permeability UVT.

Further, the second measuring unit is preferably disposed to be spaced apart from the second irradiation unit so that the displacement amount of the ultraviolet ray permeability UVT due to the deterioration of the second irradiation unit and the second measuring unit becomes equal to or less than an allowable error, as in a positional relation between the irradiation unit 15 and the ultraviolet ray monitor windows 802 and 803 provided in the UV-irradiation apparatus 800 according to the third embodiment.

The second irradiation unit preferably irradiate the treatment water with the ultraviolet rays for calculating at the time of inspection of the UV-irradiation apparatuses 1, 800 and 1000. Thus, it is possible to retard the deterioration of the second irradiation units due to the irradiation of ultraviolet rays.

Furthermore, the controllers 132 and 1002 (the calculators) are also capable of detecting the deterioration of the irradiation unit 15 and the ultraviolet ray monitor 12*a*, using the ultraviolet ray permeability UVT calculated on the basis of the ultraviolet ray intensity of ultraviolet rays emitted from the irradiation unit 15 and the ultraviolet ray intensity measured by the ultraviolet ray monitor 12*a*, and the ultraviolet ray permeability UVT calculated on the basis of the ultraviolet ray intensity of ultraviolet rays emitted from the second irradiation unit and the ultraviolet ray intensity measured by the second measuring unit. Furthermore, the controllers may also correct the measurement result of ultraviolet ray intensity by the ultraviolet ray monitor 12*a*, based on the detection result of the deterioration of the ultraviolet ray monitor 12*a*.

As described above, according to the first to fourth embodiments, since there is no need to provide a dedicated measuring device capable of measuring the ultraviolet ray permeability, it is possible to calculate the ultraviolet ray permeability of the treatment water at a low cost and with a simple configuration.

Further, a program executed by the UV-irradiation apparatuses 1, 800 and 1000 of this embodiment is provided by being previously incorporated in a ROM or the like. Moreover, the program executed by the UV-irradiation apparatuses 1, 800 and 1000 according to this embodiment may be configured so that the program is provided by being recorded on a computer-readable recording medium such as a CD-ROM, a flexible disk (FD), a CD-R and a digital versatile disk (DVD), by a file of an installable format or an executable format.

Furthermore, the program executed by the UV-irradiation apparatuses 1, 800 and 1000 of this embodiment may be configured so that the program is stored on a computer connected to a network such as the Internet and is provided by being downloaded via a network. Further, the program executed by the UV-irradiation apparatuses 1, 800 and 1000 of this embodiment may also be configured so that the program is provided or distributed via a network such as the Internet.

The program executed by the UV-irradiation apparatuses 1, 800 and 1000 of this embodiment has a module configuration that includes the above-described each unit (the controllers 132 and 1002), and as an actual hardware, a CPU (a processor) reads and executes the program from the ROM, each of the units is loaded on the main memory device, and the controllers 132 and 1002 are generated on the main memory device.

While some embodiments of the present invention have been described, these embodiments are presented as examples and are not intended to limit the scope of the present invention. These new embodiments are capable of being embodied in various other forms, and various omissions, substitutions and modifications can be made within the scope that does not depart from the gist of the invention. These embodiments and their modifications fall within the scope and gist of the invention and fall within the invention as set forth in the claims and their equivalent scopes.

The invention claimed is:

1. A UV-irradiation apparatus comprising:
    a first irradiation unit and a second irradiation unit that irradiate treatment water with ultraviolet rays respectively having a first ultraviolet ray intensity and a second ultraviolet ray intensity;
    a first measuring unit that is associated with the first irradiation unit and a second measuring unit that is associated with the second irradiation unit, the first measuring unit and the second measuring unit respectively measuring a third ultraviolet ray intensity and a fourth ultraviolet ray intensity of ultraviolet rays transmitted through the treatment water, wherein
        the first measuring unit is spaced relative to a first central axis of the first irradiation unit and the second measuring unit is spaced relative to a second central axis of the second irradiation unit at a predetermined liquid phase distance that is based on
            a preset allowable error of ultraviolet ray permeability of the treatment water and
            a predetermined value that indicates when treatment performance to the treatment water cannot be maintained;
    a detecting unit that detects deterioration of the first irradiation unit and the second irradiation unit in accordance with the third ultraviolet ray intensity and the fourth ultraviolet ray intensity respectively measured by the first measuring unit and the second measuring unit;
    a calculator that calculates the ultraviolet ray permeability of the treatment water, on the basis of the first ultraviolet ray intensity and the second ultraviolet ray intensity of ultraviolet rays respectively emitted from the first irradiation unit and the second irradiation unit depending on a preset setting value and the third ultraviolet ray intensity and the fourth ultraviolet ray intensity respectively measured by the first measuring unit and the second measuring unit; and
    a display that displays an ultraviolet ray monitor indication value indicative of a detection result of the deterioration of the first irradiation unit and the second irradiation unit by the detecting unit, and an ultraviolet ray permeability value, distinct from the ultraviolet ray monitor indication value, indicative of the ultraviolet ray permeability calculated by the calculator, wherein:
        the predetermined liquid phase distance allows the ultraviolet ray permeability to be obtained when a displacement amount of the ultraviolet ray permeability due to deterioration associated with the first irradiation unit is equal to or less than the preset allowable error; and
        the predetermined liquid phase distance allows the ultraviolet ray permeability to be obtained when the displacement amount of the ultraviolet ray permeability due to deterioration associated with the second irradiation unit is equal to or less than the preset allowable error.

2. The UV-irradiation apparatus according to claim 1, wherein the detecting unit further detects the deterioration of the first irradiation unit and the second irradiation unit in accordance with the ultraviolet ray permeability calculated by the calculator.

3. The UV-irradiation apparatus according to claim 1, wherein:
    the first measuring unit is further disposed to be spaced apart from the first central axis of the first irradiation unit so that the displacement amount of the ultraviolet ray permeability is equal to or less than the preset allowable error when the third ultraviolet ray intensity measured by the first measuring unit is lowered to the predetermined value in which a treatment performance to the treatment water cannot be maintained; and the second measuring unit is further disposed to be spaced apart from the second central axis of the second irradiation unit so that the displacement amount of the ultraviolet ray permeability is equal to or less than the preset allowable error when the fourth ultraviolet ray intensity measured by the second measuring unit is lowered to the predetermined value in which a treatment performance to the treatment water cannot be maintained.

4. The UV-irradiation apparatus according to claim 1, wherein the calculator calculates a first effective irradiation intensity and a second effective irradiation intensity of ultraviolet rays respectively emitted from the first irradiation unit and the second irradiation unit, and a first effective transmission intensity and a second effective transmission intensity respectively measured by the first measuring unit and the second measuring unit, on the basis of the permeability of ultraviolet rays with respect to the treatment water measured by an external measuring device, and calculates the ultraviolet ray permeability on the basis of the first and second effective irradiation intensities and the first and second effective transmission intensities.

5. A UV-irradiation apparatus comprising:

a first irradiation unit and a second irradiation unit that irradiate treatment water with ultraviolet rays respectively having a first ultraviolet ray intensity and a second ultraviolet ray intensity;

a first measuring unit that is associated with the first irradiation unit and a second measuring unit that is associated with the second irradiation unit, the first measuring unit and the second measuring unit respectively measuring a third ultraviolet ray intensity and a fourth ultraviolet ray intensity of the ultraviolet rays transmitted through the treatment water, wherein the first measuring unit is spaced relative to a first central axis of the first irradiation unit and the second measuring unit is spaced relative to a second central axis of the second irradiation unit at a predetermined liquid phase distance that is based on a preset allowable error of ultraviolet ray permeability of the treatment water and a predetermined value that indicates when treatment performance to the treatment water cannot be maintained;

a detecting unit that detects deterioration of the first irradiation unit and the second irradiation unit in accordance with the third ultraviolet ray intensity and the fourth ultraviolet ray intensity respectively measured by the first measuring unit and the second measuring unit;

a calculator that calculates the ultraviolet ray permeability of the treatment water, using a preset setting value, and a ratio of the third ultraviolet ray intensity and the fourth ultraviolet ray intensity respectively measured by the first measuring unit and the second measuring unit to the first ultraviolet ray intensity and the second ultraviolet ray intensity of the ultraviolet rays respectively emitted from the first irradiation unit and the second irradiation unit in accordance with the setting value, on the basis of the following formula; and a display that displays a numerical ultraviolet ray monitor indication value indicative of detection results of the deterioration of the first irradiation unit and the second irradiation unit by the detecting unit, and a numerical ultraviolet ray permeability value indicative of the ultraviolet ray permeability calculated by the calculator, $$UVT = A \times \ln(B \times S/D)$$

wherein:

UVT is a numerical ultraviolet ray permeability value, S is a ratio of at least the third ultraviolet ray intensity or the fourth ultraviolet ray intensity respectively measured by the first measuring unit and the second measuring unit to at least the first ultraviolet ray intensity or the second ultraviolet ray intensity of ultraviolet rays respectively emitted from the first irradiation unit and the second irradiation unit depending on the setting value, D is a ratio representing the setting value, and A and B are predetermined coefficients, the predetermined liquid phase distance allows the ultraviolet ray permeability to be obtained when a displacement amount of the ultraviolet ray permeability due to deterioration associated with the first irradiation unit is equal to or less than the preset allowable error, and the predetermined liquid phase distance allows the ultraviolet ray permeability to be obtained when the displacement amount of the ultraviolet ray permeability due to deterioration associated with the second irradiation unit is equal to or less than the preset allowable error.

* * * * *